United States Patent [19]

Nolph

[11] 4,133,891

[45] Jan. 9, 1979

[54] PERITONEAL DIALYSIS SOLUTION CONTAINING NITROPRUSSIDE

[75] Inventor: Karl D. Nolph, Columbia, Mo.

[73] Assignee: The Curators of the University of Missouri, Columbia, Mo.

[21] Appl. No.: 781,630

[22] Filed: Mar. 28, 1977

[51] Int. Cl.$^2$ ............................................. A61K 31/295
[52] U.S. Cl. ...................................... 424/295; 128/213
[58] Field of Search .......................... 424/295; 128/213

[56] References Cited

PUBLICATIONS

Nolph et al.; Trans. Amer. Soc. Artif. Int. Organs, (1976), pp. 586–594, vol. XXII.

Primary Examiner—Allen J. Robinson
Attorney, Agent, or Firm—Ray E. Snyder

[57] ABSTRACT

A peritoneal dialysis solution containing the vasodilating drug nitroprusside which is effective to increase peritoneal clearances and thereby permit a significant reduction in the time devoted to the performance of a dialysis procedure.

4 Claims, 3 Drawing Figures

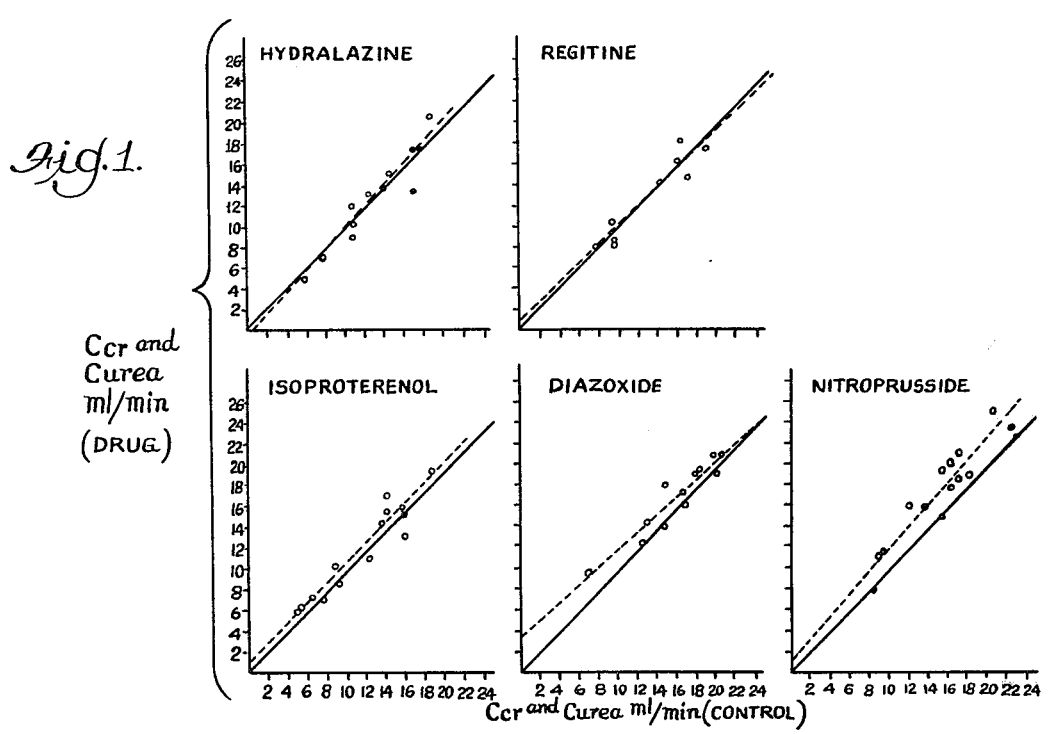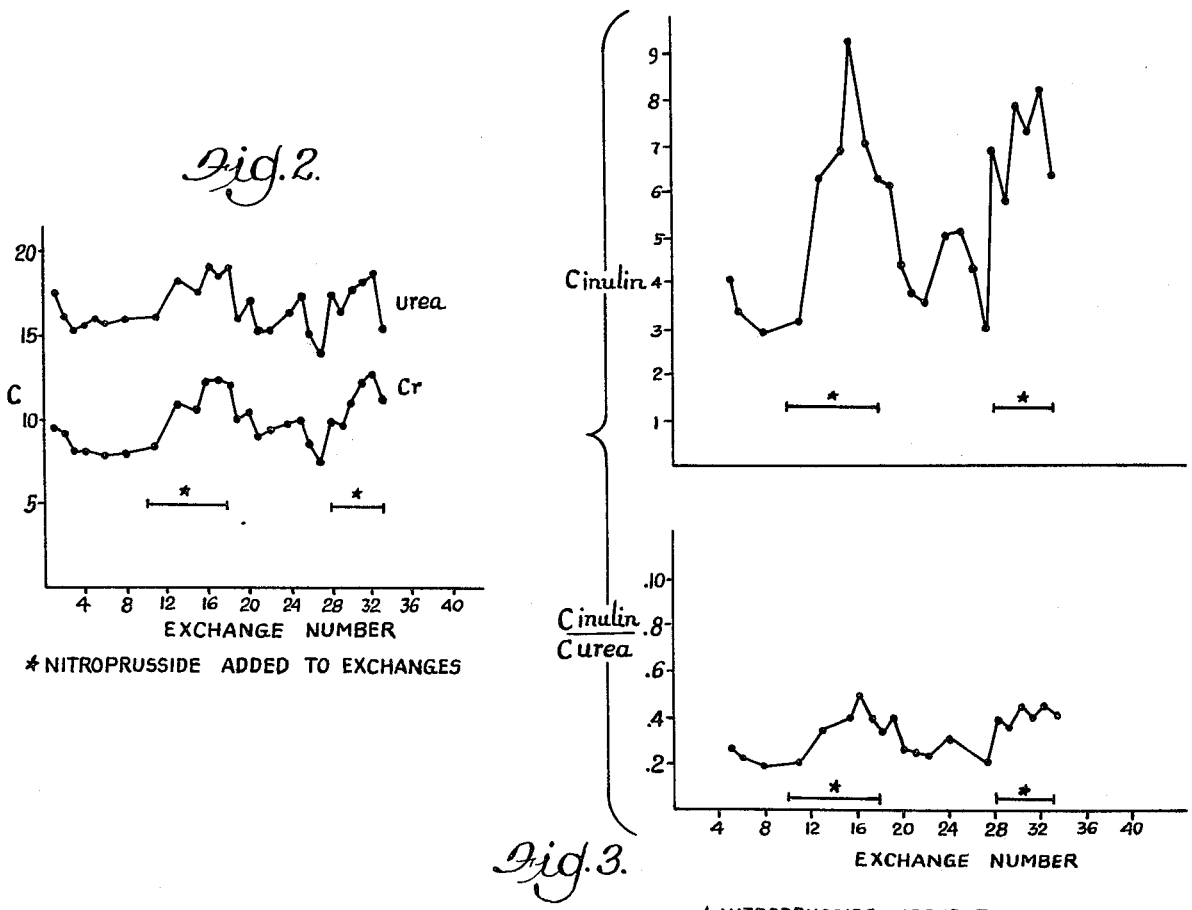

PERITONEAL DIALYSIS SOLUTION CONTAINING NITROPRUSSIDE

BACKGROUND OF THE INVENTION

The invention described and claimed herein was made in the course of work under a grant or award from the Department of Health, Education, and Welfare.

FIELD OF THE INVENTION

The invention relates generally to the field of Surgery, and more particularly to drug containing solutions for use in performing peritoneal dialysis within a patient.

DESCRIPTION OF THE PRIOR ART

Peritoneal dialysis at present requires 36 hrs/wk or more to maintain maximum concentrations of serum urea and creatinine below levels maintained with 18 hrs/wk or less of extracorporeal dialysis. Compared to extracorporeal dialysis, the low peritoneal dialysis clearances of smaller solutes, such as urea (60 daltons) and creatinine (113 daltons), reflect peritoneal dialysate flow and possibly peritoneal blood flow limitations. The clearances of larger solutes, such inulin (5000 daltons), are similar in peritoneal dialysis and extracorporeal dialysis. Clearances of these larger solutes are limited mainly by membrane area and permeability. Although the relative importance of removing small solutes (less than 500 daltons) or larger "middle molecular" solutes (500-5000 daltons) is currently being debated, most centers do demand some reasonable control of small solute blood levels, as reflected by creatinine and urea concentrations. (Scientific references for supporting the above statements are to be found in Vol. XXII Trans. Amer. Soc. Artif. Int. Organs, 1976).

The effective peritoneal blood flow available for solute exchange with peritoneal dialysis solution is unknown. The fact that dialysate to plasma concentration ratios for urea and creatinine are often 0.60 or less, at dialysis solution flow rates of 30 ml/min, suggests blood flow limitations on clearances in addition to the obvious dialysate flow limitation.

The effects of vasodilator drugs on the visceral and parietal peritoneal capillary beds should be accomplished with small amounts of drugs in dialysis solution, yielding relatively high local concentrations, adjacent to and within the peritoneal membrane. These responses should be achieved with minimal systemic effects. Slow absorption of such drugs and the obligatory passage of absorbed drug through the portal venous system to the liver, should result in minimal concentrations in the systemic circulation. If vasodilators merely increase capillary flow, clearances should increase relatively more for smaller, highly diffusable (blood flow limited) solutes. Any associated changes in capillary permeability and/or increases in the total capillary area available for exchange, may influence the clearances of the larger molecular weight solutes as well.

SUMMARY OF THE INVENTION

It is an object of the present invention to provide an improved peritoneal dialysis solution containing the vasodilating drug nitroprusside.

BRIEF DESCRIPTION OF THE DRAWINGS

FIG. 1 shows a plurality of graphs plotting mean predrug exchange clearances of creatinine and urea as related to mean drug exchange clearances for a number of vasodilating drugs;

FIG. 2 is a graph plotting clearances of urea and creatinine for a plurality of exchanges using nitroprusside; and FIG. 3 is a graph showing the effect of the addition of nitroprusside on inulin clearance and on the inulin/urea ratio.

DETAILED DESCRIPTION OF THE PREFERRED EMBODIMENT

EXAMPLES

Thirty-four studies were performed in seven patients with chronic renal failure in the Clinical Research Center of the University of Missouri Medical Center. Studies consisted of:

A. three control pre-drug exchanges;
B. three exchanges with a vasodilator added; and
C. three post-drug exchanges.

Each exchange consisted of 2000 ml of standard peritoneal dialysis solution, containing 1.5% dextrose, 140 mEq/L sodium, 101 mEq/L chloride, 45 mEq/L acetate, 1.5 mEq/L magnesium, and 4 mEq/L calcium. KCL, 3 mEq/L, was added to most exchanges. Exchanges were instilled over 10 mins, allowed to dwell for 30 mins, and drained by gravity for 30 mins. The prolonged drainage period was to assume as complete drainage as possible.

Studies were performed with 5 vasodilator drugs. The drugs, the number of studies and the amount of drugs added to a 2 L exchange (only one drug/exchange/study) were:

hydralazine, a direct vasodilator — six studies, 20–40 mgs;
phentolamine (Regitine) an alpha blocker — five stds, 5 mgs;
isoproterenol, a beta stimulator — eight studies, 0.12 mgs;
diazoxide, a direct vasodilator — seven studies, 100–300 mgs;
nitroprusside, a direct vasodilator — eight studies, 6–12 mgs;

Drug doses/exchange did not exceed amounts that could be given intravenously over a time period equal to that of the exchange. Nevertheless, all doses should have given relatively high local concentrations.

Blood samples were drawn at the beginning of every third exchange throughout dialysis. Dialysate was drained by gravity and the volume of drainage measured for every exchange.

Concentrations of urea and creatinine were determined in all serum and dialysate samples, using the Technicon Autoanalyzer II. Concentrations of urea and creatinine were also determined in peritoneal dialysis solutions, prior to instillation, both with and without the addition of the drugs to be studied in order to test for possible interference by glucose or drugs with chemical measurements. In special studies inulin clearances were performed as described below and inulin concentrations in serum and dialysate measured.

CALCULATIONS

The mean drainage volume from over 300 exchanges was determined as 2191 ± 244 ml (standard deviation). Data from study exchanges in which the drainage volume did not fall within one standard deviation of this mean drainage wolume were excluded from analyses. Serum clearances of urea ($C_{urea}$) and creatinine ($C_{cr}$) were calculated in ml/min as: (dialysate concentration/serum concentration) × (drainage volume/time). Serum concentrations used were those actually measured at or extrapolated to the beginning of each exchange.

For each study, mean clearances of pre-drug control exchanges (the three exchanges immediately preceding drug containing exchanges), the mean clearances of the exchanges containing drug and the post-drug control exchanges (three exchanges immediately following drug exchanges) were calculated. Studies were performed at various times during peritoneal dialysis. Sometimes as many as three studies were performed during a 48 hour peritoneal dialysis. Differences between mean clearances for pre-drug control exchanges and drug exchanges for all studies with each drug were tested for significance by a paired $t$ analysis.

CLINICAL MEASUREMENTS AND CONTROLS

During all drug free exchanges, blood pressure (first and fifth phase) and pulse were recorded in the supine position at least one (mid-point) during every exchange. During drug containing exchanges, blood pressure and pulse were recorded twice (beginning and mid-point) during every exchange. Fluid and sodium intake during these studies were such as to approximate any net negative losses by urine and dialysis to as to permit minimal weight changes during the studies. Any medications with know vascular or blood pressure effects were withheld during the studies. Studies were started at a variety of different times during peritoneal dialysis so as to randomly distribute eating and drinking periods throughout the studies. To further assess possible effects of stress, eating, and many other variable in a clinical setting, on peritoneal blood flow (and thereby perhaps on clearances) in one patient clearances were followed throughout a dialysis utilizing only drug free exchanges.

RESULTS

Urea and creatinine concentrations in dialysis solution pre-infusion (1500 mg% glucose) (tested as a blank) were negligible with maximum concentrations for urea nitrogen being 0.0 mg% and for creatinine 0.56 mg%. The actual creatinine blank reading would even be less in actual drainage following absorption of some of the glucose. None of the drugs added to dialysis solutions in the concentrations used interfered with the methods and thereby, increased these "blank" concentrations.

The results of the studies are set forth in the graphs of FIG. 1 which show mean control clearances of creatinine and urea and respective mean clearances for drug containing exchanges in all 34 studies. Mean pre-drug exchange clearances of creatinine (open circles) and urea (closed circles) are shown on the horizontal axes and related to mean drug exchange clearances on the vertical axes. Linear regressions (dashed lines) and correlation coefficients are shown for each drug. Solid lines represent identity lines. For hydralazine and regitine, points were scattered evenly about the identity line and the linear regression closely approximates the identity line. For isoproterenol, diazoxide, and nitroprusside, the majority of points fall above the identity line. Differences of these points from the identity line for mean urea clearances were significant for isoproterenol ($p < 0.05$), diazoxide ($p < 0.025$), and nitroprusside ($p < 0.01$). For creatinine clearances, differences from the identity line were significant for isoproterenol ($p < 0.05$) and nitroprusside ($p < 0.01$).

Because of the finding with nitroprusside, and additional study was performed during a single peritoneal dialysis in one patient. After a series of nine control exchanges, nine consecutive exchanges containing nitroprusside were performed. These were followed by nine additional drug-free exchanges, which were then in turn followed by six additional exchanges, containing nitroprusside. For all nitroprusside containing exchanges, 9 mgs of drug were added to each 2 L exchange. Prior to this study, a loading dose of inulin was administered. Since the renal function in this patient during dialysis was negligible, serum inulin levels decreased very slowly during peritoneal dialysis. In addition to determinations of urea and creatinine clearances/exchange as above, inulin clearances were determined.

Significant increases in creatinine clearances were seen for nitroprusside. The $C_{cr}$ to $C_{urea}$ ratios remained essentially stable even when clearances increased. There were no significant changes in heart rate. Significant decreases in systolic blood pressure and diastolic blood pressure were seen following the use of diazoxide. With nitroprusside, significant decreases in diastolic blood pressure during the nitropursside exchanges were seen. For hydralazine, diazoxide, and nitroprusside, dose variation in the range given did not correlate with clearance changes suggesting maximum local effects were achieved at all doses.

FIGS. 2 and 3 show the results when longer series of consecutive exchanges with nitroprusside were studied, each preceded by six control exchanges. FIG. 2 shows modest increases in urea and creatinine clearance, with a tendency to return to baseline following withdrawal of the nitroprusside exchanges. Clearances increased again when drug containing exchanges were used. Most striking are the clearance changes seen for inulin in the same study. Clearances more than doubled compared to control during nitroprusside exchanges and return to baseline following withdrawal of the drug containing exchanges. Clearances again more than doubled during reinstitution of drug containing exchanges.

For all studies, the mean ratios of dialysate to serum concentrations and the mean drainage volumes were calculated and mean differences analyzed statistically as for all the above clearance data. Significant differences in clearances above were paralleled by significant differences in the ratio of dialysate to serum concentrations. No significant differences in drainage volume during or after isoproterenol, Regitine, or hydralazine, were observed, as set forth in Table I. With nitroprusside, drainage volume increased in six of eight studies by a mean value of 65 ml ($p < 0.05$). A volume increase of this magnitude could account for clearance increases of less than 1 ml/min. With diazoxide no significant differences were observed between mean pre-drug and drug values. Mean volumes for post-drug exchanges were less than respective pre-drug values in six of six studies ($p < 0.025$) with the overall mean value decreasing by 78 ml.

TABLE I.

| Drug | No. of Studies | Pre-Exchange No. | Pre-Exchange Volume | Drug Exchanges No. | Drug Exchanges Volume | Post-Exchanges No. | Post-Exchanges Volume |
|---|---|---|---|---|---|---|---|
| Nitroprusside | 8 | 22 | 2121±37 | 29 | 2186±36* | 14 | 2180±31 |
| Diazoxide | 7 | 15 | 2139±22 | 20 | 2185±49 | 19 | 2075±20+ |
| Isoproterenol | 8 | 19 | 2164±36 | 26 | 2194±16 | 18 | 2153±30 |
| Phentolamine (Regitine) | 5 | 12 | 2194±41 | 12 | 2229±16 | 11 | 2173±59 |
| Hydralazine | 6 | 16 | 2209±12 | 13 | 2205±29 | 14 | 2227±30 |

*p <0.05 compared to pre-exchanges
+p <0.025

The results of these and previous studies suggest that significant increases in clearances with isoproterenol, diazoxide, and nitroprusside may be realized. Nitroprusside showed the most consistent and greatest effects. With nitroprusside, mean increases in urea clearances were near 3 ml/min. Although clearance increases of this magnitude may seem rather modest, increases of 20–25% could shorten the time required to reduce a serum urea nitrogen concentration to a given level (all other factors being stable), by as much as 6 to 8 hrs. At the dialysate flow rates of these studies (30 ml/min), clearances are still primarily limited by dialysate flow rate.

The increases in urea and creatinine clearances seen with vasodilators in these studies are not, however, likely to be explained by simple increases in blood flow rate to peritoneal capillaries. Creatinine and urea clearances increased proportionately and $C_{cr}$ to $C_{urea}$ ratios remained unchanged. Simple increases in capillary flow should have proportionately greater effects on clearnaces of the more diffusable urea. The stable $C_{cr}$ to $C_{urea}$ ratio suggests an associated effect on area or permeability. In addition, the very large proportional increases in inulin clearances seen with nitroprusside suggest an effect on membrane permeability characteristics. Slight increases in drainage volume could not account for clearance changes but may reflect also increased capillary hydrostatic pressure, and/or permeability. Thus, although effects of increasing peritoneal capillary flow cannot be excluded, increases in membrane area and/or permeability must have occurred.

Our findings suggest mainly local effects since changes in heart rate did not occur and changes in blood pressure seen with only two drugs were very modest. It is interesting that with nitroprusside, blood pressure decreased only during the nitroprusside containing exchanges in association with increased clearances. Such findings would be most compatible with local splanchnic vasodilation. With diazoxide in contrast, blood pressure decreased following withdrawal of the drug and at a time when clearances were usually decreasing. These findings could be explained by delayed absorption, systemic vasodilation and resulting decreases in peritoneal blood flow. Associated decreases in drainage volume might reflect decreased capillary hydrostatic pressure associated with reduced peritoneal blood flow.

The fact that similar changes were not seen with all vasodilators is of interest and several possible explanations can be mentionyd. First, binding of a drug in the peritoneum may impair diffusion to receptor sites for its action on the peritoneal vasculature. Secondly, effects could differ because of differences in sensitivity of the peritoneal vasculature to these drugs. Thirdly, it is possible that the increases in clearances seen may represent unique permeability effects independent of vasodilation.

For clinical purposes, the data suggest that only moderate increases in small solute clearances can be anticipated with the addition of these vasodilators. Nevertheless, 25% increases as seen in some patients would permit the more rapid reduction of small solute concentrations. Perhaps even more important are the suggested proportionately greater increases in the clearances of solutes in the higher molecular weight range. There is currently much interest in the removal of solutes in this molecular weight range, with indirect evidence that some uremic toxins, particularly those associated with uremic neuropathy, may fall in this category. If such is the case, our data suggest that peritoneal dialysis could remove these solutes at rates more rapidly than hemodialysis. For example, baseline inulin clearance with extracorporeal dialysis is around 5 ml/min with most dialyzers. Although baseline peritoneal clearances are similar, with nitroprusside, peritoneal clearances increased more than twice that of the baseline value.

In none of the exchanges using nitroprusside was there any evidence of peritoneal irritation or cloudiness of the drained fluid. Some preliminary studies were also conducted with the I. V. administration of nitroprusside to reduce the systolic and/or diastolic pressure 10 mm Hg. There was no evidence of any effect whatsoever on peritoneal clearances when nitroprusside was used systemically. This tends to confirm that the nitroprusside has some effect on permeability that is independent of its normal vasodilating properties.

The invention is not to be considered as limited to the embodiment described, except insofar as the claims hereto may be so limited.

I claim:

1. A peritoneal dialysis fluid containing the following ingredients in the approximate concentration of:
   140 mEq/L sodium
   101 mEq/L chloride
   45 mEq/L acetate
   1.5 mEq/L magnesium
   4 mEq/L calcium; and
the vasodilating drug nitroprusside in the approximate concentration of 3 to 6 mg. per liter.

2. A method for increasing peritoneal dialysis clearances within a patient surgically fitted with an indwelling catheter comprising the steps of:
   providing a dialysis fluid having in solution the ingredients in the concentrations as follows:
   140 mEq/L sodium
   101 mEq/L chloride
   45 mEq/L acetate
   1.5 mEq/L magnesium
   4 mEq/L calcium; and adding the vasodilating drug nitroprusside in the approximate concentration of 3 to 6 mg. per liter to the dialysis fluid defined; and infusing said modified dialysis fluid into a patient through the indwelling catheter.

3. The peritoneal dialysis fluid of claim 1 including: 3 mEq/L potassium chloride as an additional ingredient.

4. The method of claim 2 including:

adding potassium chloride in the approximate concentration of 3 mEq/L to the dialysis fluid.

* * * * *